United States Patent [19]

Blumenthal

[11] 4,453,634
[45] Jun. 12, 1984

[54] DISPENSER PACK

[75] Inventor: Klaus Blumenthal, Leubsdorf, Fed. Rep. of Germany

[73] Assignee: Lohmann GmbH & Co. KG, Neuwied, Fed. Rep. of Germany

[21] Appl. No.: 411,679

[22] Filed: Aug. 26, 1982

[30] Foreign Application Priority Data

Sep. 3, 1981 [DE] Fed. Rep. of Germany ... 8125693[U]

[51] Int. Cl.³ .......................................... B65D 85/671
[52] U.S. Cl. .................................... 206/389; 206/409; 206/411; 220/4 B; 220/353; 242/197
[58] Field of Search ............... 206/389, 396, 397, 398, 206/400, 401, 402, 403, 408, 409, 410, 411, 225, 438, 439, 440, 441, 363; 220/307, 353; 242/71.1, 197

[56] References Cited

U.S. PATENT DOCUMENTS

| | | | |
|---|---|---|---|
| 585,645 | 7/1897 | Achenbach | 206/440 |
| 1,013,715 | 1/1912 | Yuste et al. | 206/407 |
| 1,357,754 | 11/1920 | Weglener | 206/440 |
| 1,826,084 | 10/1931 | Mohr | 206/409 |
| 1,869,729 | 8/1932 | Zuckerman | 206/409 |
| 1,967,187 | 7/1934 | Dickson | 206/409 |
| 2,340,024 | 1/1944 | Skaller | 206/440 |
| 3,190,517 | 6/1965 | Rice | 206/409 |
| 3,252,568 | 5/1966 | Steidinger | 206/403 |
| 4,219,119 | 8/1980 | Zefran | 220/253 |
| 4,256,225 | 3/1981 | Jackson | 206/409 |

FOREIGN PATENT DOCUMENTS

| | | | |
|---|---|---|---|
| 1119575 | 3/1982 | Canada | 242/77.1 |
| 1496934 | 8/1967 | France | 220/353 |
| 368741 | of 1932 | United Kingdom | 206/409 |

Primary Examiner—George E. Lowrange
Assistant Examiner—Jimmy G. Foster
Attorney, Agent, or Firm—Becker & Becker, Inc.

[57] ABSTRACT

A dispenser pack for accommodating strip or tape-like packaged material in roll form. The dispenser pack includes a bottom with integrally molded, axially parallel side walls, a removable lid which is parallel to the bottom, and an outlet or removal slot. A wall portion is molded onto the lid. This wall portion has the same length as the side walls, one of which is provided with a recess into which the wall portion, which is slightly narrower than the recess, extends asymmetrically, while leaving free the removal slot and at the same time forming a fixing gap for the packaged material.

8 Claims, 3 Drawing Figures

DISPENSER PACK

The present invention relates to a dispenser pack for accommodating strip or tape-like packaged material in roll form, and comprises a bottom with integrally molded, axially parallel side walls, a removable lid which is parallel to the bottom, and an outlet or removal slot.

Dispenser packs of this general type are known for films, adhesive tapes, or the like wound onto cores. In this case, the film or foil-like packaged material is wound tightly so that an inherently stable roll aligning itself inside the pack is provided on the core. As a result of the core, this roll retains its shape until the packaged material is completely removed.

In contrast thereto, it is an object of the present invention to devise a dispenser pack for relatively soft or pliable strip-like packaged material which is not very inherently stable, such as swabs, muslin or gauze bandages, dressing material, or the like, which is kept in roll form without a core and can be removed from the dispenser pack. At the same time, it is intended to ensure that the soft packaged material, before use, is always maintained readily accessible within the removal slot, without it being necessary to open the dispenser pack.

These and other objects and advantages of the present invention will appear more clearly from the following specification in connection with the accompanying drawing, in which.

Figure 1:
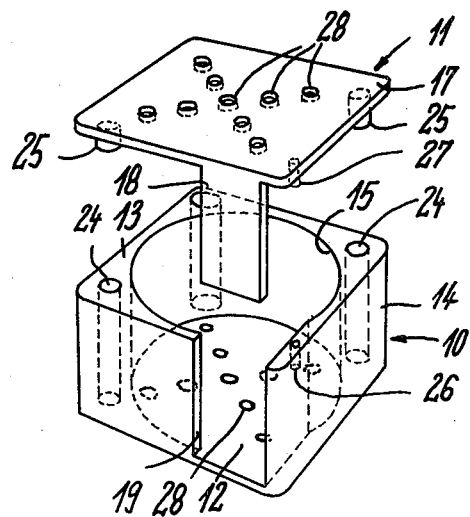
FIG. 1 shows one inventive embodiment of an opened dispenser pack.

The dispenser pack of the present invention is characterized primarily in that a wall portion is molded onto the lid; this wall portion has the same length as the side walls, one of which is provided with a recess into which the wall portion, which is slightly narrower than the recess, extends asymmetrically, while leaving free the removal slot and at the same time forming a fixing gap for the packaged material.

The dispenser pack thus comprises two parts which form a dimensionally stable, shock-resistant housing which is not sensitive to pressure. This housing advantageously has a parallelepipedal outer contour, and the side walls have an inner contour adapted to the shape of the roll. The dispenser pack is thus suitable for accommodating soft packaged material which is not very inherently stable, such as bandaging-material swabs, surgical gauze, or the like. The rolled-up, strip-like packaged material does not require a core inside the dispenser pack. After inserting the roll into the bottom part (formed via the bottom and the side walls), the free end of the roll is pulled outwards through the removal slot and is returned inside the recess in such a way that, after placement of the lid part, the wall portion which extends asymmetrically into the recess retains the free end of the packaged material in the fixing gap, while the adjoining portion of the packaged material leads outwardly beyond the wall portion into the removal slot. This has the advantage that the free end of the roll is always held ready in the removal slot, and during sterilizing, transport, and storage the roll is held in place to some extent by the clamped free end. During the initial removal of bandaging material it is unnecessary to open the dispenser pack. Moreover, the free end can be pulled out of the fixing gap, and the desired length can then be withdrawn easily and without resistance from the removal slot.

The lid part is advantageously secured to the bottom part by a snap-fastener system, wherein in at least two diametrically opposite corners of the side walls holes are provided between the outer contour and the inner contour, into which holes it is possible to insert correspondingly shaped studs or pins provided on the lid.

It is also possible, in the vicinity of the removal slot, to provide an additional smaller hole in one of the side walls between the outer contour and the inner contour; a corresponding pin on the lid can be inserted into this hole.

The bottom and the lid have numerous perforations which ensure the steam permeability of the dispenser pack during the sterilization process in the autoclave. For this purpose, the dispenser pack is advantageously made of synthetic material which is resistant to sterilization and to high temperatures. This synthetic material is preferably translucent, so that it is always possible to see how much bandaging material is still available.

The dispenser may comprise two injection-molded parts of thermoplastic synthetic material.

The dispenser pack is stackable, and takes up a particularly small amount of space. Also, because of its inherent stability, the dispenser pack is suitable for first-aid boxes, first-aid sets, and the like.

Referring now to the drawing in detail, the dispenser pack essentially comprises a bottom part 10 and a lid part 11.

The bottom part 10 has a bottom or base 12 and a side wall 13. The side wall 13 forms, together with the bottom part 12 and the lid part 11, a parallelepipedal outer contour 14 of the dispenser pack. The side wall 13, which is molded on the base 12, has an inner contour 15 which is adapted to the roll shape or to the outside of the roll of packaged material 16. For greater clarity, in FIG. 3 the as yet unused packaged material roll 16 is shown substantially smaller than the inner contour 15.

Figure 2:
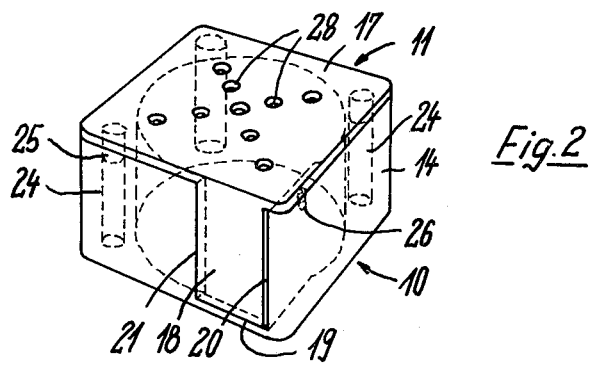
FIG. 2 shows a closed dispenser pack in a perspective view.

The lid part 11 comprises a removable lid 17 which is parallel to the bottom 12 and has a molded-on wall portion 18. The wall portion 18 has the same length as the rest of the side wall 13, which is provided with a recess 19. The recess 19 is slightly wider than the wall portion 18. The wall portion 18 is inserted asymmetrically into the recess 19 (FIG. 2), whereby a removal slot 20 is left free for the packaged material 16. On the other side of the wall portion 18, a fixing gap 21 for the free end 22 of the packaged material 16 is thus formed.

Figure 3:
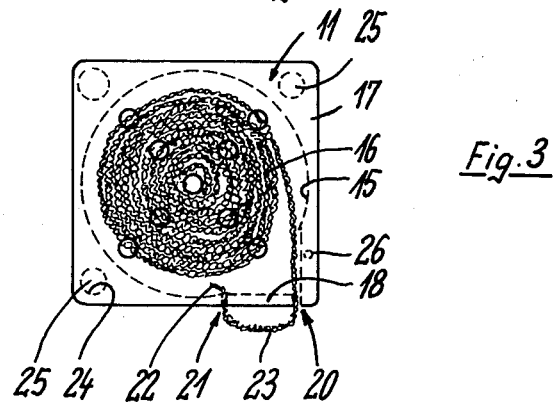
FIG. 3 is a top view of a filled dispenser pack.

As evident from FIG. 3, upon inserting the packaged material roll 16 into the bottom part 10, the free end portion of the packaged material is arranged in the form of a bight 23 which extends outwards beyond the wall portion 18 and then passes through the removal slot 20. The soft or pliant packaged material 16 is guided unobstructed in the removal slot 20.

In the exemplary embodiment illustrated, for securing the lid part 11 to the bottom part 16, holes 24 are provided in two diametrically opposed corners of the side wall 13 between the outer contour 14 and the inner contour 15. Correspondingly shaped studs or pins 25 on the lid 17 can be inserted into these holes 24. In the illustrated exemplary embodiment, the holes 24 are cylindrical bores, and the studs 25 are correspondingly shaped cylindrical pins. In this way, a snap-fastener system is created, which can be further reinforced by providing, in the vicinity of the removal slot 20, an additional smaller hole 26 in the side wall 13 into which a corresponding pin 27 on the lid 17 can be inserted.

The base 12 and the lid 17 are provided with numerous perforations 28 which, after the dispenser pack has been closed, enable the packaged material 16 to be sterilized with steam in an autoclave. In this case, it is also advantageous for the free end 22 of the packaged material roll 16 to be held securely in the fixing gap 21.

Preferably, the base part 10 and the lid part 11 are one-piece injection-molded parts consisting of a thermoplastic synthetic material. The synthetic material is resistant to sterilization and to high temperatures. Translucent synthetic materials are preferably used.

The present invention is, of course, in no way restricted to the specific disclosure of the specification and drawing, but also encompasses any modifications within the scope of the appended claims.

What I claim is:

1. A dispenser pack for accommodating relatively soft and pliable strip or tape-like packaged material which is not very inherently stable, such as swabs, muslin or gauze bandage dressing materials or the like kept packaged in roll for without a core though removable from the dispenser pack where the soft material is always maintained readily removable without necessity to open the dispenser pack, said dispenser pack comprising a bottom part which includes a base and axially parallel side walls integrally molded to one another and to said base, one of said side walls being provided with a recess; and a lid part adapted to be removably placed on said bottom part, said lid part including a lid which is parallel to said base, and a wall portion which is molded onto said lid and projects toward said base when said lid part is placed on said bottom part; said wall portion of said lid part having the same length as said side walls and being slightly narrower than said recess; said wall portion, when said lid part is placed on said bottom part, extending asymmetrically into said recess in such a way as to leave free a permanently open removal slot for said packaged material, and in such a way as to form an additional fixing gap for always holding ready an end of said packaged material during sterilization, transport, and storage thereof.

2. A dispenser pack according to claim 1, in which said dispenser pack, when closed, has a parallelepipedal outer contour, and in which said side walls have an inner contour adapted to the shape of said roll of packaged material.

3. A dispenser pack according to claim 2, in which at least two diametrically opposite corners of said side walls are provided with holes between said outer contour and said inner contour; and in which correspondingly shaped pins are provided on said lid, said pins being inserted in respective ones of said holes when said lid part is placed on said bottom part.

4. A dispenser pack according to claim 3, in which one of said side walls, in the vicintiy of said removal slot, is provided with an additional smaller hole between said outer contour and said inner contour; and in which a correspondingly shaped additional pin is provided on said lid, said additional pin being inserted in said additional hole when said lid part is placed on said bottom part.

5. A dispenser pack according to claim 3, in which said base and said lid are provided with numerous perforations.

6. A dispenser pack according to claim 5, in which said bottom part and said lid part are injection-molded parts of thermoplastic synthetic material.

7. A dispenser pack according to claim 5, in which said bottom part and said lid part are made of synthetic material which is resistant to sterilization and to high temperatures.

8. A dispenser pack according to claim 7, in which said synthetic material is translucent.

* * * * *